US008916189B2

(12) United States Patent
Watanabe et al.

(10) Patent No.: US 8,916,189 B2
(45) Date of Patent: Dec. 23, 2014

(54) CELL CULTURE SUPPORT FOR FORMING STRING-SHAPED CARDIOMYOCYTE AGGREGATES

(75) Inventors: Masanao Watanabe, Tokyo (JP); Teruo Okano, Tokyo (JP); Masayuki Yamato, Tokyo (JP); Tatsuya Shimizu, Tokyo (JP); Yoshikatsu Akiyama, Tokyo (JP)

(73) Assignees: Dai Nippon Printing Co., Ltd., Tokyo (JP); Tokyo Women's Medical University, Tokyo (JP)

( * ) Notice: Subject to any disclaimer, the term of this patent is extended or adjusted under 35 U.S.C. 154(b) by 1740 days.

(21) Appl. No.: 12/122,194

(22) Filed: May 16, 2008

(65) Prior Publication Data

US 2008/0293139 A1    Nov. 27, 2008

(30) Foreign Application Priority Data

May 22, 2007   (JP) ................................. 2007-135659

(51) Int. Cl.
*A61F 2/00* (2006.01)
*C12N 5/02* (2006.01)
*C12N 5/077* (2010.01)
*C12N 5/00* (2006.01)

(52) U.S. Cl.
CPC ............ *C12N 5/0657* (2013.01); *C12N 5/0068* (2013.01); *C12N 2533/30* (2013.01); *C12N 2535/10* (2013.01)
USPC .......................................... 424/426; 435/404

(58) Field of Classification Search
USPC .......................................... 424/426; 435/404
See application file for complete search history.

(56) References Cited

U.S. PATENT DOCUMENTS

| 2005/0042254 A1* | 2/2005 | Freyman et al. ............. 424/426 |
| 2007/0048292 A1 | 3/2007 | Morita et al. |
| 2007/0190645 A1 | 8/2007 | Miyake et al. |
| 2007/0218554 A1 | 9/2007 | Miyake et al. |
| 2008/0124795 A1 | 5/2008 | Miyake et al. |

FOREIGN PATENT DOCUMENTS

| JP | 02-211865 B2 | 8/1990 |
| JP | 6-104061 B2 | 12/1994 |
| JP | 2004-170935 A | 6/2004 |
| JP | 2005-168494 A | 6/2005 |
| JP | 2006-346292 A | 12/2006 |
| WO | 2005/085413 A1 | 9/2005 |
| WO | 2005/085414 A1 | 9/2005 |
| WO | 2005/103227 A1 | 11/2005 |

OTHER PUBLICATIONS

Japanese Office Action issued May 10, 2011 in counterpart Japanese Application No. 2007-135659.
Koh-Ichiro Kinugawa, et al.; "Transcriptional Regulation of Inducible Nitric Oxide Synthase in Cultured Neonatal Rat Cardiac Myocytes"; Circulation Research; 1997; pp. 911-921; vol. 81; American Heart Association Inc.
Tatsuya Shimizu, et al.; "Fabrication of Pulsatile Cardiac Tissue Grafts Using a Novel 3-Dimensional Cell Sheet Manipulation Technique and Temperature-Responsive Cell Culture Surfaces"; Circulation Research; Feb. 22, 2002; pp. 1-9; vol. 90, No. 3; e40-e48; American Heart Association Inc.

* cited by examiner

*Primary Examiner* — Ruth Davis
(74) *Attorney, Agent, or Firm* — Sughrue Mion, PLLC

(57) ABSTRACT

This invention is intended to provide cell aggregates that can reproduce functions of the myocardium, such as the function of beating, and thus are available for myocardial regenerative therapy, and to provide a cell culture support for producing the same.

According to this invention, a cell culture support for forming string-shaped cardiomyocyte aggregates, which has a substrate portion having one surface on which at least one linear cell-adherent region is formed is provided.

7 Claims, 4 Drawing Sheets

(a)

US 8,916,189 B2

CELL CULTURE SUPPORT FOR FORMING STRING-SHAPED CARDIOMYOCYTE AGGREGATES

CLAIM OF PRIORITY

The present application claims priority from Japanese application JP 2007-135659 filed on May 22, 2007, the content of which is hereby incorporated by reference into this application.

BACKGROUND OF THE INVENTION

1. Field of the Invention

The present invention relates to a cell culture support for forming string-shaped beating cardiomyocyte aggregates and a method for forming string-shaped cardiomyocyte aggregates with the use of the same.

2. Background Art

A method whereby somatic stem cells (tissue stem cells) represented by myelocytes are selected and transplanted (injected) directly into the heart of a patient, has been studied as a method for cardiomyocyte transplantation and myocardial regenerative therapy. In addition, there have been studies regarding the induction of efficient differentiation of ES cells (embryonic stem cells) of non-human mammals into cardiomyocytes. In recent years, there have also been studies regarding the efficient induction of differentiation of tissue stem cells (e.g., undifferentiated cells contained in fatty tissue) into cardiomyocytes. Thus, the range of cells that are used as sources for cardiomyocyte transplantation and myocardial regenerative therapy has been expanding. However, a technique for artificially constructing tissue having functions of the myocardium, such as the function of beating, has not yet been established.

A variety of cell culture supports for forming a sheet-type cell aggregate used for regenerative medicine and the like have been available (e.g., JP Patent Publication (Kokai) No. 2004-170935 A, JP Patent Publication (Kokai) No. 2005-168494 A, and JP Patent Publication (Kokoku) No. 6-104061 B (1994)). However, cardiomyocyte sheets produced by the above techniques do not have the function of beating. In the case of a cardiomyocyte sheet prepared with the use of a conventional cell culture support comprising primary cardiomyocytes (cells released from connective tissue (collected from a baby rat) by collagenase treatment), cardiomyocytes account for half of cells dispersed therein, and vascular endothelial cells, fibroblast cells, and the like account for the other half thereof. A single cardiomyocyte that serves as a pacemaker cell can be found in approximately 10,000 cardiomyocytes. Cells are electrically connected to each other via a gap junction on a cardiomyocyte sheet formed in a random manner. In such case, when cells are connected to each other, the pathway for beating is established in a manner such that electric signals generated from a plurality of pacemaker cells are transmitted through cardiomyocytes and the other cells. In the case of a sheet comprising confluent cells, synchronization takes place via the shortest pathway including pacemaker cells. However, in such case, electric signal emission lacks direction. Thus, during beating, the entire sheet repeatedly dilates and contracts; however such dilation and contraction lack direction.

SUMMARY OF THE INVENTION

In the case of the heart, the direction of transmission of action potentials generated at the sinoatrial node and the direction of contraction of left and right ventricles and atriums are predetermined. Thus, it has been necessary to provide myocardial tissue that can beat in a single direction. Therefore, it is an objective of the present invention to provide cell aggregates that can reproduce functions of the myocardium, such as the function of beating, and thus are available for myocardial regenerative therapy, and to provide a cell culture support for producing the same.

In order to achieve the above objective, the present inventors conducted intensive studies. As a result, they have found that myocardial tissue, in which cells are connected to each other in the longitudinal direction such that they form a string shape having a width of one to several tens of cells, has the function of beating in a single direction. Such string-shaped myocardial tissue can securely transmit a virtual cardiac potential generated from a pacemaker cell or an external electrode in the longitudinal direction of such string. In addition, the present inventors have found the structure of a cell culture support that is appropriate for forming cardiomyocyte aggregates having the above shape and the function.

The present invention encompasses the following inventions.

(1) A cell culture support for forming string-shaped cardiomyocyte aggregates, which has a substrate portion having one surface on which at least one linear cell-adherent region is formed.

(2) The cell culture support according to (1), wherein the width of the linear cell-adherent region is 1 to 19 times wider than that of a cell to be cultured.

(3) The cell culture support according to (1), wherein the width of the linear cell-adherent region is 5 to 40 μm.

(4) The cell culture support according to any one of (1) to (3), wherein a plurality of linear cell-adherent regions are formed on one surface and a non-cell-adherent region is formed between each two of the plurality of linear cell-adherent regions.

(5) The cell culture support according to (4), wherein the distance between neighboring cell-adherent regions is 30 μm or more.

(6) The cell culture support according to (4) or (5), wherein a plurality of convex ridge portions each having a cell-adherent upper surface are formed and a concave groove is formed between each two of the convex ridge portions on one surface, such concave groove having a non-cell-adherent inner surface.

(7) The cell culture support according to any one of (1) to (6), wherein the linear cell-adherent region is a linear region on one surface in which an environmentally-responsive high molecular compound is arranged, such compound having cell adhesion properties under cardiomyocyte culture conditions.

(8) A method for forming string-shaped cardiomyocyte aggregates, comprising the step of culturing cardiomyocytes on a substrate portion of the cell culture support according to any one of (1) to (7).

(9) A string-shaped cardiomyocyte aggregate, which is formed by the method according to (8).

(10) A cell culture support carrying adhering cardiomyocyte aggregates, comprising the cell culture support according to any one of (1) to (7) and string-shaped cardiomyocyte aggregates that have adhered to a cell-adherent region on the surface of a substrate portion of the cell culture support.

String-shaped cardiomyocyte aggregates that have been formed with the use of the cell culture support of the present invention transmit action potentials in the longitudinal direction thereof, have the function of beating, and can dilate and contract in the longitudinal direction.

Figure 1A:
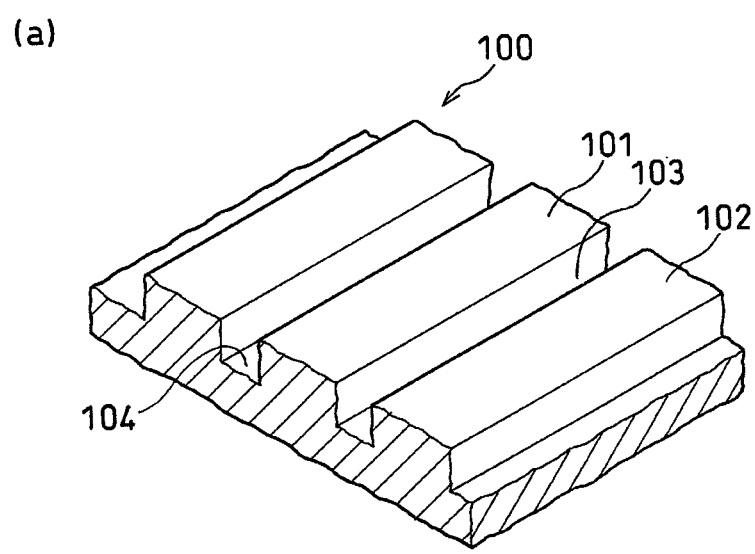
FIG. 1a is an enlarged perspective view of a part of a substrate portion in one embodiment of the cell culture support of the present invention, such substrate portion having one surface on which a plurality of convex ridge portions each having a flat cell-adherent upper surface and concave grooves formed between such plurality of convex ridge portions are formed.

The numerals in the figures have the following meanings.
100, 110 . . . Substrate portion
101 . . . Convex ridge portion
102 . . . Upper surface (cell-adherent region) of a convex ridge portion
103 . . . Concave groove
104 . . . Bottom surface of a concave groove
111 . . . Cell-adherent region
112 . . . Non-cell-adherent region

DESCRIPTION OF THE PREFERRED EMBODIMENTS

The cell culture support for forming string-shaped cardiomyocyte aggregates of the present invention has a substrate portion on one side thereof, such substrate portion having at least one linear cell-adherent region formed thereon.

Examples of material of a substrate portion include glasses, plastics, ceramics, and metals, which are generally used for cell culture. As long as cell culture can be carried out, such material is not limited to the above examples. An arbitrary layer may be provided on the surface or an intermediate layer of a substrate portion unless it hinders the objective of the present invention. Alternatively, an arbitrary treatment may be carried out. For instance, it is possible to make the surface of a substrate portion hydrophilic by a treatment technique involving ozone treatment, plasma treatment, sputtering, or the like.

The overall shape of the cell culture support may be any shape as long as the cell culture support has a substrate portion having specific features of the present invention and is appropriate for the purposes of cell culture. For instance, a sheet-type substrate consisting of a substrate portion, a culture dish (petri dish) having a substrate portion and a sidewall portion formed around the circumference of the substrate portion, and the like can be used.

According to the present invention, at least one linear cell-adherent region is formed on at least one side of the above substrate. Such linear cell-adherent region is not particularly limited as long as it is in a linear form, and thus it may be in a straight line form, a curved form, a broken curved form, or any combination thereof. The curvature of a curved portion is not necessarily constant. Cardiomyocyte aggregates are formed along the cell-adherent region.

Preferably, the width of a linear adherent region is 1 to 19 times wider than the width of a cell to be cultured. A specific value of the width of a linear adherent region is preferably 5 to 40 µm. The length of a linear adherent region is not particularly limited. However, it is preferably 5 mm to 750 mm and particularly preferably 10 mm to 300 mm.

In a preferred embodiment, a plurality of linear cell-adherent regions are formed on one surface of a substrate portion and a non-cell-adherent region is formed between each two of the plurality of linear cell-adherent regions. With the use of the cell culture support of such embodiment, many cell aggregates can be obtained at once. This is because a plurality of string-shaped cell aggregates are formed on a plurality of linear cell-adherent regions such that neighboring cell aggregates are isolated from each other via a non-cell-adherent region so as not to be connected to each other. The distance between neighboring cell-adherent regions is not particularly limited as long as the distance does not allow cells that form myocardium tissue to be crosslinked to each other. However, such distance is preferably 30 µm or more and more preferably 40 µm or more.

A cell-adherent region can be formed by treating a desired region on a substrate portion by an adequate method so as to make the region cell-adherent. Alternatively, in a case in which the surface of a substrate itself has cell adhesion properties, the surface of a substrate itself can be used as a cell-adherent region. It is known that cells generally tend to adhere to a hydrophobic surface. In addition, a variety of methods are known as methods for imparting cell adhesion properties to the surface of a base material. A particularly preferable treatment method is a method for forming a cell-adherent region by coating the surface of a substrate with an environmentally-responsive high molecular compound in a linear form, such polymer being cell-adherent under cardiomyocyte culture conditions and becoming non-cell-adherent upon environmental change in terms of temperature, pH, ion concentration, and the like. It is possible to coat the surface of a base material portion with a temperature-responsive high molecular compound in a linear form by a conventional microfabrication technique.

Preferred examples of an environmentally-responsive high molecular compound include temperature-responsive polymers, pH-responsive polymers, and ion-responsive polymers. Among them, temperature-responsive polymers are the most preferable.

It is preferable that a temperature-responsive polymer that can be preferably used for the present invention to be hydrophobic at a cell culture temperature (approximately 37° C. in general) and to be hydrophilic at a temperature for collection of a culture cell sheet. In addition, the temperature at which a temperature-responsive polymer changes from being hydrophobic to hydrophilic (critical solution temperature (T) in water) is not particularly limited. However, in view of ease of collection of cultured cell aggregates, such temperature is preferably lower than a cell culture temperature. With the presence of such temperature-responsive polymer component, a cell scaffold (cell adhesion surface) is sufficiently secured upon cell culture so that cell culture can be efficiently carried out. Meanwhile, upon collection of cultured cell aggregates, hydrophobic portions become hydrophilic so that cultured cell aggregates are removed from a cell culture base material. Thus, collection of cell aggregates can be further facilitated.

Specifically, a temperature-responsive polymer that can be preferably used for the present invention is a polymer having the above "T" of 0° C. to 80° C. and preferably of 0° C. to 50° C. When T exceeds 80° C., cells might be killed, which is not preferable. In addition, when T is lower than 0° C., cell growth rate is extremely lowered or cell are killed in general, which is not preferable. Examples of the above preferable polymer include a polymer described in JP Patent Publication (Kokoku) No. 6-104061 B (1994).

Specific examples of an appropriate polymer include poly-N-isopropylacrylamide (T=32° C.), poly-N-n-propylacrylamide (T=21° C.), poly-N-n-propylmethacrylamide (T=32° C.), poly-N-ethoxyethyl acrylamide (T=approximately 35° C.), poly-N-tetrahydrofurfuryl acrylamide (T=approximately 28° C.), poly-N-tetrahydrofurfuryl methacrylamide (T=approximately 35° C.), and poly-N,N-diethylacrylamide (T=32° C.). In addition, examples of such polymer include: poly-N-ethylacrylamide; poly-N-isopropylmethacrylamide; poly-N-cyclopropylacrylamide; poly-N-cyclopropylmethacrylamide; poly-N-acryloylpyrrolidine; poly-N-acryloylpiperidine; polymethylvinyl ether; alkyl-substituted cellulose derivatives such as methylcellulose, ethylcellulose, and hydroxypropylcellulose; polyalkylene oxide block copolymers represented by a block copolymer of polypropyleneoxide and polyethyleneoxide; and polyalkylene oxide block copolymers.

The above polymers are prepared by homopolymerization or copolymerization of a monomer that constitutes a homopolymer having T of 0° C. to 80° C. Examples of such monomer include a (meth)acrylamide compound, an N-(or N,N-di)alkyl-substituted (meth)acrylamide derivative, a (meth)acrylamide derivative having a ring group, and a vinyl ether derivative. At least one such example may be used. In addition, monomers other than the above examples may be added for copolymerization when it is necessary to control T depending on the type of cell to be grown, when it is necessary to improve interaction between a coating material and a cell culture support, or when it is necessary to adjust the hydrophilic-hydrophobic balance of a cell support. Further, it is also possible to use a graft or block copolymer of the polymer used for the present invention and other polymers or a mixture of the polymer of the present invention and other polymers. In addition, it is also possible to crosslink polymers as long as the original properties of polymers are not impaired.

A pH-responsive polymer and an ion-responsive polymer can be adequately selected, provided that they are appropriate for a cell aggregate to be prepared.

The coating amount of a different environmentally-responsive high molecular compound in a cell-adherent region is 5 to 80 μg/cm$^2$ and preferably 6 to 40 μg/cm$^2$. When the coating amount of a high molecular compound exceeds 80 μg/cm$^2$, cells do not adhere to the surface of a cell culture support. On the other hand, when the coating amount is less than 5 μg/cm$^2$, cells are cultured in a single layer and do not form a tissue. In such case, it is difficult to remove and collect culture cells from a support. Such coating amount of a high molecular compound can be determined by, for example, the Fourier-transform infrared attenuated total reflection spectroscopy (the FT-IR-ATR method), analysis involving staining of a coated portion or an uncoated portion or staining with a phosphor, surface analysis involving contact angle measurement, or any combination thereof.

As a method for coating the surface of a substrate portion with an environmentally-responsive high molecular compound, chemical methods and physical methods can be used alone or in combination. When the above monomer is used upon coating, the monomer may be in a gaseous, liquid, or solid form. In addition, when a polymer is used, the polymer may also be in a liquid or solid form. When such compound is allowed to bind to the polymer or monomer by a chemical reaction, electron beam irradiation (EB), γ-ray irradiation, ultraviolet irradiation, plasma treatment, or corona treatment can be used. Further, when the material of the surface of a substrate portion and a coating material have an appropriate reactive functional group, an organic reaction that is generally used for radial and ion reactions and the like can be used. An example of a method that utilizes physical interaction is, but is not limited to, a method involving coating, kneading, or the like that causes physical adsorption with the use of a coating material alone or a medium that is a matrix compatible to the material of the surface of a substrate portion.

A non-cell-adherent region can be formed by treating a desired region on the surface of a substrate portion by an adequate method and processing the treated region such that the region becomes cell-adherent. Alternatively, when the surface of a substrate portion itself is non-cell-adherent, the surface of a substrate portion itself can be used as a non-cell-adherent region. It is known that cells are generally unlikely to adhere to a hydrophilic surface. In addition, there are different known treatment methods whereby cell adhesion properties are imparted to the surface of a base material. A particularly preferable treatment method is a method for forming a non-cell-adherent region by coating the surface of a substrate with a hydrophilic high molecular compound in a linear form. It is possible to coat the surface of a substrate with a hydrophilic high molecular compound in a linear form with the use of a generally used microfabrication technique.

Examples of a hydrophilic high molecular compound include: natural products such as natural high molecular proteins, including BSA (bovine serum albumin), and natural high molecular sugar chains, including chitin/chitosan and hyaluronic acid; and synthetic molecular compounds such as polymers comprising polymerized alkylene glycol, including polyethylene glycol and polyethylene oxide, polyacrylamide, a tryblock polymer known as Pluronic used for polyethylene glycol treatment, different amino acid polymers, and polysiloxane (provided as a hydrogel to the surface of a substrate portion or provided thereto for silane treatment). Examples of a method for coating the surface of a substrate include: a method wherein a hydrophilic high molecular compound is allowed to be adsorbed by the surface of a substrate by immersion, casting, or the like with the use of interaction between a hydrophobic portion or a hydrophilic portion of a polymer chain of a hydrophilic high molecular compound and the surface of a substrate; and a method wherein a chemical bond is formed between the surface of a substrate portion and a hydrophilic high molecular compound with the use of a silane coupling agent or via graft polymerization such that hydrophilicity of the surface can be maintained for a long term. In the Examples described herein, a hydrophilic polymer surface is prepared by carrying out electron beam graft polymerization of an acrylamide monomer on the surface of a substrate.

Next, a specific embodiment of a substrate portion on which a plurality of linear cell-adherent regions and a plurality of linear non-cell-adherent regions are alternately arranged is described based on the drawings.

FIG. 1a shows an embodiment of a substrate portion. A substrate portion (100) comprises, on one surface thereof, a plurality of convex ridge portions (101) each having an upper surface (102) and concave grooves (103) separately formed between each two of the convex ridge portions. Every upper surface (102) is cell-adherent so that a linear cell-adherent region is formed thereon. The inner surface of a concave groove (103) is non-cell-adherent so that a non-cell-adherent region is formed thereon. In the embodiment of the present invention, a non-cell-adherent concave groove (103) serves as an obstacle so as to prevent a string-shaped cardiomyocyte aggregate (formed on each upper surface (102)) from connecting to another one in the latitudinal direction. The width and length of the upper surface correspond to the width and length of linear cell-adherent regions. Thus, the size of the upper surface can be selected with a width and a length appropriate for that of a linear cell-adherent region. The aforementioned method is used as a method for imparting cell adhesion properties to an upper surface. The form of a convex ridge portion is not limited to a straight line form shown in FIG. 1a, and thus it may be any of the above-described different line forms of a cell-adherent region, such as a curved form, a broken curved form, or any combination thereof. The cross section of a concave groove is not limited to the rectangle form shown in FIG. 1a, and thus it may be a V-shaped form, a U-shaped form, a semicircular arch form, a trapezoidal form, a reverse trapezoidal form, or the like. The aforementioned method is used as a method for making the inner surface of a concave groove non-cell-adherent. The width of the opening of a concave groove (i.e., the distance between convex ridge portions) is not particularly limited in terms of size as long as the width does not allow cells that form a myocardium tissue to be crosslinked with each other. Such width is preferably 30 µm or more and more preferably 40 µm or more. Methods for forming convex ridge portions and concave grooves are not particularly limited. Thus, a microfabrication technique known to persons skilled in the art can be used.

Figure 3:
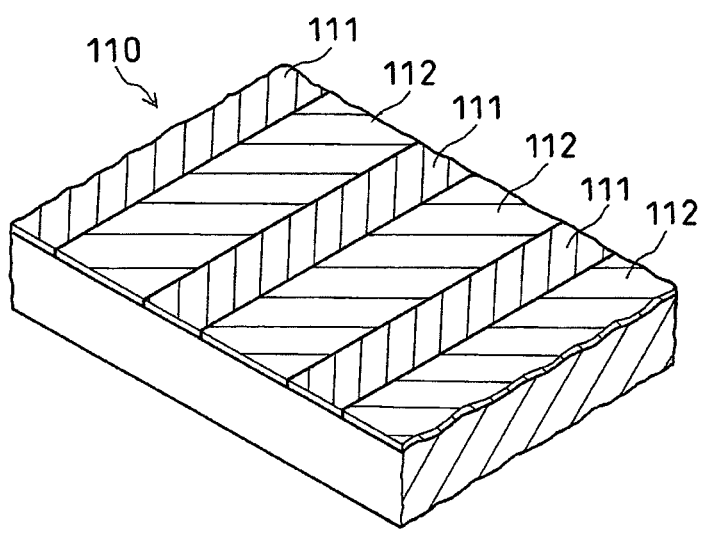
FIG. 3 is an enlarged perspective view of a part of a substrate portion in another embodiment of the cell culture support of the present invention, such substrate portion having one smooth surface on which linear cell-adherent regions and a plurality of non-cell-adherent regions are alternately arranged.

FIG. 3 shows another embodiment of a substrate portion. FIG. 3 is an enlarged perspective view of a substrate portion (110) having one smooth surface on which a plurality of linear cell-adherent regions (111) and a plurality of non-cell-adherent regions (112) are alternately arranged. In this embodiment of the present invention, a non-cell-adherent region (112) serves as an obstacle so as to prevent a plurality of string-shaped cardiomyocyte aggregates (formed on linear cell-adherent regions (111)) from connecting to each other in the latitudinal direction. A method for forming a cell-adherent region (111) and a non-cell-adherent region (112) and the sizes of such regions are as described above.

Next, a method for forming string-shaped cardiomyocyte aggregates with the use of the above cell culture support is described below.

Preferably, primary cardiomyocytes prepared by a conventional method are used as cardiomyocytes to be cultured. Such primary cardiomyocytes that can be used are cells collected from a newborn of a mammal such as rat and subjected to connective tissue treatment with collagenase. As a method for preparing primary cardiomyocytes, known methods described in different papers can be used (e.g., primary newborn rat cardiomyocytes described in Kinugawa K, Shimizu T, Yao A, Kohmoto O, Serizawa T, Takahashi T. Transcriptional regulation of inducible nitric oxide synthase in cultured neonatal rat cardiac myocytes. Circ Res. 1997; 81: 911-921). Cardiomyocytes to be cultured may be mixed with non-cardiomyocytes (e.g., vascular endothelial cells and fibroblast cells) as long as a cultured cell aggregate has functions of myocardial tissue.

Cardiomyocytes can be cultured by adding an appropriate medium to a vessel having the above cell culture support on the bottom thereof and seeding cardiomyocytes on it, followed by culture. Cardiomyocyte aggregates are formed within 3 to 4 days, in general. When cardiomyocytes to be cultured are mixed with non-cardiomyocytes, functions of the cardiomyocytes might be inhibited as a result of excessive growth of non-cardiomyocytes after a long culture period. Thus, a culture period is preferably approximately 1 week or less.

Typically, the string-shaped cardiomyocyte aggregate of the present invention formed with the use of the above cell culture support has a diameter of 5 to 40 µm and a length of 1 to 30 cm. The string-shaped cardiomyocyte aggregate of the present invention has the function of beating and dilates and contracts in the longitudinal direction of the string, and thus it can be used for myocardial regeneration.

It is also possible to provide a product that is a complex (referred to as a "cell culture support carrying adhering cardiomyocyte aggregates") comprising a cell culture support and string-shaped cardiomyocyte aggregates adhering to a cell-adherent region of the surface of the substrate portion of the culture support. The aggregates are to be removed from the cell culture support. In the cell culture support carrying adhering cardiomyocyte aggregates of the present invention, the shape of a cardiomyocyte aggregate adhering to a substrate portion is maintained so that it is suitable for being carried.

EXAMPLES

Preparation of Cell Culture Supports

In each Examples 1 to 8, a cell culture support shown in FIG. 1a was formed in a manner such that it had a substrate (100) on one surface of which a plurality of convex ridge portions (101) were formed and concave grooves (103) were formed between the convex ridge portions (101). Each convex ridge portion had a flat upper surface (102) coated with a cell-adherent temperature-responsive polymer.

Figure 1B:
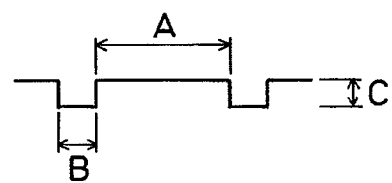
FIG. 1b shows definitions of the width of a convex ridge portion, the distance between convex ridge portions (or the width of a concave groove), and the depth of a concave groove.
Figure 2:
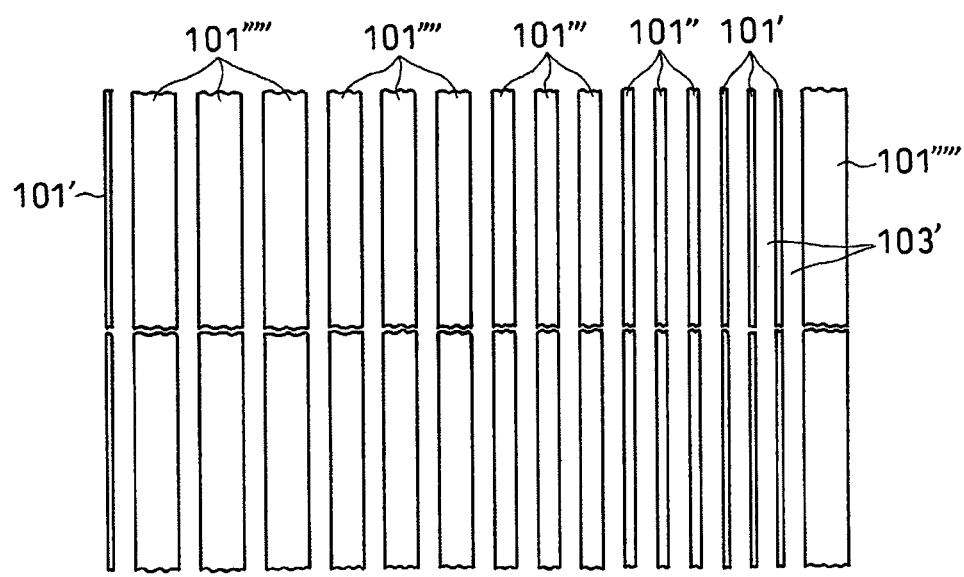
FIG. 2 shows a top view of a substrate portion of the cell culture support of Example 7.

Specifically, a plurality of convex ridge portions having the widths shown in table 1 (A, FIG. 1b) were formed in parallel to each other at the relevant intervals as shown in table 1 (B, FIG. 1b) on the surface of a rectangle substrate 45 mm in length and 20 mm in width. In each Example, concave grooves were formed with two different depths of 4 µm and 8 µm (C, FIG. 1c). In Example 7, five types of convex ridge portions having different widths were formed on the surface of a single substrate. In Example 7, the interval between convex ridge portions was fixed at 20 µm. FIG. 2 shows a top view of the substrate of Example 7. In Example 8, a plurality of convex ridge portions each having a width of 20 µm were formed in parallel to each other at five different intervals on the surface of a single substrate.

In the Comparative example, a cell culture support was prepared in the same manner as in Examples 1 to 8, except that a fine convex-concave pattern was not formed on a substrate.

TABLE 1

|  | Pattern | With of convex ridge portion (A) (µm) | Interval between convex ridge portions (B) (µm) |
| --- | --- | --- | --- |
| Example 1 | Stripe | 20 | 30 |
| Example 2 | Stripe | 20 | 20 |
| Example 3 | Stripe | 20 | 10 |
| Example 4 | Stripe | 10 | 30 |
| Example 5 | Stripe | 10 | 20 |
| Example 6 | Stripe | 10 | 10 |
| Example 7 | Convex ridge portions having five different widths | 5, 10, 20, 30, 40 | 20 |
| Example 8 | Convex ridge portions arranged at five different intervals | 20 | 5, 10, 20, 30, 40 |
| Comparative example | None | — | — |

In Examples 1 to 8, fine pattern processing was carried out in accordance with the procedures described in JP Patent Publication (Kokai) No. 2005-84561 A (Example 2). Each cell culture support was produced by forming convex ridge portions (101) comprising the following molding resin composition on a soda glass plate with the use of a resist plate. The procedures are described in detail below.

A photoresist layer 4 µm in thickness was formed by single spin coating of a photoresist (product name: "AZ5218," Clariant (Japan) K. K.) on a synthetic quartz plate 6.35 mm in thickness having a Cr layer 0.11 µm in thickness formed thereon. Further, a double-layered photoresist layer 8 µm in thickness was formed thereon by spin coating with a photoresist of the same type. The resulting plate was exposed in a predetermined pattern with the use of an EV-620 mask aligner (EVG) and then processed with the use of a TOK-NMD3 developer (Tokyo Ohka Kogyo Co., Ltd.), resulting in the formation of a resist pattern. Thus, a resist plate (primary plate) was formed thereon. Subsequently, the surface of the resist plate was coated with a UV-photosensitive molding resin (product name: "SEL-XC," The Inctec Inc.). Ultraviolet irradiation was carried out from the resin side thereof with the use of a high pressure mercury lamp under conditions of 170 mJ/cm$^2$ (365 nm) such that the molding resin was cured. Thus, a resin plate (secondary plate) was formed thereon. The resist plate and the resin plate were removed therefrom. Then, ultraviolet irradiation was carried out again from the convex-concave side with the use of a high pressure mercury lamp under conditions of 170 mJ/cm$^2$ (365 nm).

The following composition was prepared as a UV-photosensitive molding resin composition used for a tertiary plate.

TABLE 2

Composition of molding resin composition

| | |
|---|---|
| Urethane acrylate (product name: GOHSELAC UV-7500B, Nippon Synthetic Chemical Industry Co., Ltd.) | 35 parts |
| 1,6-hexanediol diacrylate (Nippon Shokubai) | 35 parts |
| Pentaerythritol triacrylate (Toagosei) | 11 parts |
| Vinyl pyrrolidone (Nippon Shokubai) | 15 parts |
| 1-hydroxy cyclohexyl phenyl ketone (product name: Irgacure 184, Ciba Specialty Chemicals) | 2 parts |
| Benzophenone (nacalai tesque) | 2 parts |
| Alcohol-denatured silicone oil (product name: TSF4570, GE Toshiba Silicones) | 1 part |

The molding resin composition of table 2 was added dropwise to the concave groove side of the molding mold prepared above. A soda glass plate 1.1 mm in thickness subjected to anchor treatment was allowed to overlap the molding mold in a manner such that the treatment side of the soda glass plate faced the molding mold. Ultraviolet irradiation was carried out from the molding mold side with the use of a high pressure mercury lamp under conditions of 170 mJ/cm$^2$ (365 nm) such that the molding resin composition therebetween was cured. Thereafter, the molding mold was removed. Then, ultraviolet irradiation was carried out again for the convex-concave side with the use of a high pressure mercury lamp under conditions of 170 mJ/cm$^2$ (365 nm). Thus, the finely patterned product shown in FIG. 1 was obtained. The pattern on the obtained finely patterned product had no missing portions. In addition, no residue of the cured molding resin composition was found in concave grooves of the removed molding mold.

In the Comparative example, a support was produced in the same manner as in Examples 1 to 8, except that a fine convex-concave pattern was not formed thereon.

The convex-concave face of the substrate prepared above was subjected to oxygen plasma treatment such that cleanliness and uniform wettability of the convex-concave face were secured. The convex-concave face of the thus obtained substrate was coated with a temperature-responsive polymer layer having cell adhesion properties under cell culture conditions in accordance with the following procedures.

An isopropyl alcohol solution (21 μl) containing N-isopropylacrylamide adjusted to 40% by weight was added to the convex-concave face of each substrate prepared above, followed by electron beam irradiation at 30 Mrad. Thus, the convex-concave face of each substrate was coated with poly-N-isopropylacrylamide. After electron beam irradiation, each substrate was washed with ion exchange water such that residual monomers and free poly-N-isopropylacrylamide was removed therefrom, followed by drying in a clean bench. Further, gas sterilization with ethylene oxide (EO) was carried out, followed by sufficient deaeration. Thus, cell culture supports were obtained.

Coating with a Hydrophilic Polymer

For comparison, a cell culture support was prepared. It was coated with polyacrylamide (a non-cell-adherent hydrophilic polymer), which was used instead of a temperature-responsive polymer exhibiting cell adhesion properties. The cell culture support coated with polyacrylamide was prepared in accordance with the above procedures except that the isopropyl alcohol solution (21 μl) containing N-isopropylacrylamide adjusted to 40% by weight was substituted with a methanol solution containing acrylamide adjusted to 20% by weight.

Formation of String-Shaped Cell Aggregates on a Cell Culture Support

Each cell culture support coated with the relevant temperature-responsive polymer was placed on the bottom of a petri dish. Then, bovine aorta vascular endothelial cells were cultured by a conventional method in the presence of 5% $CO_2$ at 37° C. (the medium used: Dulbecco's Modified Eagle Medium (DMEM), 10% of which comprised fetal calf serum (FCS)).

On day 5 of culture, each petri dish containing a cell culture support to which a vascular endothelial cell aggregate had adhered was placed in a chamber in the presence of 5% $CO_2$ at 20° C. Adhesion of most of the cells to the upper surfaces of convex ridge portions was microscopically observed. As a result of temperature change, string-shaped cell aggregates regarding which cell-to-cell adhesion was observed were removed, provided that the number of cells arranged in the width direction of the string-shaped cell aggregates corresponded to the width of the upper surface. Cell adhesion across a concave groove was observed in some of the grooves 8 μm in depth and in many of the grooves 4 μm in depth. Table 3 lists the results of each experiment.

TABLE 3

| | Width of a convex ridge portion (μm) | Interval between convex ridge portions (μm) | Depth of a concave groove (μm) | Results |
|---|---|---|---|---|
| Example 1-1 | 20 | 30 | 4 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 500-μm area. |

TABLE 3-continued

| | Width of a convex ridge portion (μm) | Interval between convex ridge portions (μm) | Depth of a concave groove (μm) | Results |
|---|---|---|---|---|
| Example 1-2 | 20 | 30 | 8 | Cell adhesion was observed mainly on the upper surface of a convex ridge portion. String-shaped cell aggregates were obtained by removing cell aggregates at a decreased temperature. Substantially no adhesion between cell aggregates formed on neighboring convex ridge portions was observed. |
| Example 2-1 | 20 | 20 | 4 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 100-μm area. |
| Example 2-2 | 20 | 20 | 8 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 500-μm area. |
| Example 3-1 | 20 | 10 | 4 | Cell adhesion was observed mainly on the upper surface of a convex ridge portion. Cells adhered to each other across a concave groove at a high frequency. A net-shaped cell aggregates were obtained by removing cell aggregates at a decreased temperature. |
| Example 3-2 | 20 | 10 | 8 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 100-μm area. |
| Example 4-1 | 10 | 30 | 4 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 500-μm area. |
| Example 4-2 | 10 | 30 | 8 | Cell adhesion was observed mainly on the upper surface of a convex ridge portion. String-shaped cell aggregates were obtained by removing cell aggregates at a decreased temperature. Substantially no adhesion between cell aggregates formed on neighboring convex ridge portions was observed. |
| Example 5-1 | 10 | 20 | 4 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 100-μm area. |

TABLE 3-continued

| | Width of a convex ridge portion (μm) | Interval between convex ridge portions (μm) | Depth of a concave groove (μm) | Results |
|---|---|---|---|---|
| Example 5-2 | 10 | 20 | 8 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 500-μm area. |
| Example 6-1 | 10 | 10 | 4 | Cell adhesion was observed mainly on the upper surface of a convex ridge portion. Cells adhered to each other across a concave groove at a high frequency. A net-shaped cell aggregates were obtained by removing cell aggregates at a decreased temperature. |
| Example 6-2 | 10 | 10 | 8 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 100-μm area. |
| Example 7-1 | 5-40 | 20 | 4 | In all patterns with 5 μm- to 40 μm-wide convex ridge portions, cell adhesion was observed on the upper surface of each convex ridge portion. String-shaped cell aggregates were obtained by removing cell aggregates at a decreased temperature. Adhesion between cell aggregates formed on neighboring convex ridge portions was observed in every 100-μm area. |
| Example 7-2 | 5-40 | 20 | 8 | In all patterns with 5 μm- to 40 μm-wide convex ridge portions, cell adhesion was observed on the upper surface of each convex ridge portion. String-shaped cell aggregates were obtained by removing cell aggregates at a decreased temperature. Adhesion between cell aggregates formed on neighboring convex ridge portions was observed in every 500-μm area. |
| Example 8-1 | 20 | 5-40 | 4 | In patterns with 5-μm and 10-μm intervals, cells adhered to each other across a concave groove at a high frequency; and a net-shaped cell aggregate was obtained by removing cell aggregates at a decreased temperature. A string-shaped cell aggregate was observed in the case of convex ridge portions with intervals of 20 μm or more. In a pattern with 40-μm intervals, substantially no adhesion between aggregates was observed. |
| Example 8-2 | 20 | 5-40 | 8 | In a pattern with 5-μm intervals, cells adhered to each other across a concave groove at a high frequency; and a net-shaped cell aggregate was obtained by removing cell aggregates at a decreased temperature. A string-shaped cell aggregate was observed in the case of convex ridge portions with intervals of 10 μm or more. In a |

TABLE 3-continued

| Width of a convex ridge portion (μm) | Interval between convex ridge portions (μm) | Depth of a concave groove (μm) | Results |
|---|---|---|---|
| | | | pattern with 30-μm intervals and a pattern with 40-μm intervals, substantially no adhesion between aggregates was observed. |
| Comparative example | — | — | — | Cell adhesion was observed in the entire surface. A cell sheet having no incisions was obtained by removing cell aggregates at a decreased temperature. |

The reason why adhesion between the formed string-shaped cell aggregates in the latitudinal direction was likely to occur in the case of a concave groove depth of 4 μm and was unlikely to occur in the case of a concave groove depth of 8 μm can be explained as follows. The steps of producing the above cell culture support include a step of washing free temperature-responsive polymer with ion exchange water. In the case of a concave groove depth of 4 μm, it is considered that almost all free temperature-responsive polymer molecules were washed away at the washing step. Meanwhile, in the case of a concave groove depth of 8 μm, it is considered that free temperature-responsive polymer molecules remained at the bottom of a concave groove after the washing step. Such remaining free temperature-responsive polymer molecules form a non-cell-adherent gel product and the surface to which the gel product has adhered becomes non-cell-adherent. Thus, in the case of a concave groove depth of 8 μm, it is assumed that concave groove portions became non-cell-adherent and thus cell adhesion between neighboring string-shaped cell aggregates was not observed. On the other hand, in the case of a concave groove depth of 4 μm, it is considered that concave groove portions became cell-adherent and thus cell adhesion between neighboring string-shaped cell aggregates was frequently observed. In order to confirm the validity of the above explanation, substrates similar to those used in Examples 1 to 8 were subjected to spray washing with ion exchange water, ultrasonic cleaning for 15 minutes, and dry sterilization. Then, bovine aorta vascular endothelial cells were cultured therein and evaluated. In the cases of the cell culture supports coated a with temperature-responsive polymer subjected to ultrasonic cleaning, cells had adhered to all the surfaces of concave grooves having a depth of 8 μm, those having a depth of 4 μm, and convex ridge portions on day 5 of culture. When the substrates were placed in a chamber in the presence of 5% $CO_2$ at 20° C., cell sheets having some incisions were removed therefrom. In addition, when the cell sheets were subjected to nuclear staining with a 25 μg/mL Hoechst 33342 ethanol solution, cell adhesion was confirmed by observation with a fluorescence wavelength of 460 nm. In view of the above, it was confirmed that the above hypothesis is reasonable.

Further, it was also attempted to culture bovine aorta vascular endothelial cells with the use of supports coated with a hydrophilic polymer, which had been subjected to spray washing with ion exchange water, ultrasonic cleaning for 15 minutes, and dry sterilization in a similar manner. However, no cells adhered to the cell culture supports coated with a hydrophilic polymer subjected to ultrasonic cleaning. When the supports were subjected to nuclear staining with a 25 μg/mL Hoechst 33342 ethanol solution, no cell adhesion was confirmed by observation with a fluorescence wavelength of 460 nm.

As a result of the above experiments, the following was confirmed. In order to obtain string-shaped cell aggregates, it is necessary that linear cell-adherent regions and linear non-cell-adherent regions be alternately arranged on the surface of a cell culture support.

Pattern Coating with a Temperature-Responsive Polymer and a Hydrophilic Polymer

Next, as in the cases of Examples 1 to 8, substrates were prepared in a manner such that the upper surface of each convex ridge portion of the substrates (having convex-concave portions formed thereon) was coated with a temperature-responsive polymer and the inner surface of each concave groove was coated with a hydrophilic polymer (by pattern coating). Specifically, the procedures of such coating are as follows.

As in the cases of Examples 1 to 8, a resist film (product name: "SUNFORT AQ1558," Asahi Kasei EMD Corporation) was laminated on the convex-concave face of each substrate (having convex-concave portions formed thereon) at 100° C., a pressure of 4 kgf/cm², and a rate of 1 m/min. Next, a negative-positive-inverted chrome mask was aligned with the prepared primary plate having the convex-concave substrate portion. Then, the upper surface of each convex ridge portion was subjected to ultraviolet irradiation with a high pressure mercury lamp under conditions of 100 mJ/cm² (365 nm). A resist film was removed from each concave groove via processing with the use of a 1% sodium carbonate aqueous solution at a temperature of 30° C. and a spray pressure of 1.5 kgf/cm² for 30 seconds. The convex-concave substrate portion having convex ridge portions each having a masked upper surface was coated with a hydrophilic polymer by the aforementioned method. Then, a mask resist was removed therefrom by washing the substrate with the use of a 3% sodium hydroxide aqueous solution. Further, the substrate was subjected to spray washing with ion exchange water, washing with ultrasonic cleaning for 15 minutes, and drying. The entire convex-concave substrate portion was coated by the above coating method with the use of a temperature-responsive polymer, followed by sufficient washing involving ultrasonic cleaning for 15 minutes and dry sterilization. The support was placed in a petri dish and bovine aorta vascular endothelial cells were cultured thereon. As a result, regardless of the depth of the convex-concave portion of the support (4 μm or 8 μm), cell adhesion was observed in a line form that did not come into contact with neighboring line forms in a pattern in which the width of a concave groove was 20 μm. In addition, when the substrate was placed in a chamber in the presence of 5% $CO_2$ at 20° C., cells that adhered in a string form were removed therefrom. Table 4 shows the results of each experiment.

TABLE 4

| | Width of a convex ridge portion (μm) | Interval between convex ridge portions (μm) | Depth of a concave groove (μm) | Results |
|---|---|---|---|---|
| Example 1-1 | 20 | 30 | 4 | Cell adhesion was observed mainly on the upper surface of a convex ridge portion. String-shaped cell aggregates were obtained by removing cell aggregates at a decreased temperature. Substantially no adhesion between cell aggregates formed on neighboring convex ridge portions was observed. |
| Example 1-2 | 20 | 30 | 8 | Cell adhesion was observed mainly on the upper surface of a convex ridge portion. String-shaped cell aggregates were obtained by removing cell aggregates at a decreased temperature. Substantially no adhesion between cell aggregates formed on neighboring convex ridge portions was observed. |
| Example 2-1 | 20 | 20 | 4 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 500-μm area. |
| Example 2-2 | 20 | 20 | 8 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 500-μm area. |
| Example 3-1 | 20 | 10 | 4 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 100-μm area. |
| Example 3-2 | 20 | 10 | 8 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 100-μm area. |
| Example 4-1 | 10 | 30 | 4 | Cell adhesion was observed mainly on the upper surface of a convex ridge portion. String-shaped cell aggregates were obtained by removing cell aggregates at a decreased temperature. Substantially no adhesion between cell aggregates formed on neighboring convex ridge portions was observed. |

TABLE 4-continued

| | Width of a convex ridge portion (μm) | Interval between convex ridge portions (μm) | Depth of a concave groove (μm) | Results |
|---|---|---|---|---|
| Example 4-2 | 10 | 30 | 8 | Cell adhesion was observed mainly on the upper surface of a convex ridge portion. String-shaped cell aggregates were obtained by removing cell aggregates at a decreased temperature. Substantially no adhesion between cell aggregates formed on neighboring convex ridge portions was observed. |
| Example 5-1 | 10 | 20 | 4 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 500-μm area. |
| Example 5-2 | 10 | 20 | 8 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 500-μm area. |
| Example 6-1 | 10 | 10 | 4 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 100-μm area. |
| Example 6-2 | 10 | 10 | 8 | Cell adhesion was observed mainly on the upper surface of a convex ridge portion. String-shaped cell aggregates were obtained by removing cell aggregates at a decreased temperature. Adhesion between cell aggregates formed on neighboring convex ridge portions was observed in every 100-μm area. |
| Example 7-1 | 5-40 | 20 | 4 | In all patterns with 5 μm- to 40 μm-wide convex ridge portions, cell ell adhesion was observed on the upper surface of each convex ridge portion. String-shaped cell aggregates were obtained by removing cell aggregates at a decreased temperature. Adhesion between cell aggregates formed on neighboring convex ridge portions was observed in every 500-μm area. |
| Example 7-2 | 5-40 | 20 | 8 | In all patterns with 5 μm- to 40 μm-wide convex ridge portions, cell adhesion was observed on the upper surface of each convex ridge portion. String-shaped cell aggregates were obtained by removing cell aggregates at a decreased temperature. Adhesion between cell aggregates formed on neighboring convex ridge portions was observed in every 500-μm area. |
| Example 8-1 | 20 | 5-40 | 4 | In a pattern with 5-μm intervals, cells adhered to each other across a concave groove at a high frequency; and a net-shaped cell aggregate was obtained by removing cell aggregates at a decreased |

TABLE 4-continued

| | Width of a convex ridge portion (μm) | Interval between convex ridge portions (μm) | Depth of a concave groove (μm) | Results |
|---|---|---|---|---|
| Example 8-2 | 20 | 5-40 | 8 | temperature. A string-shaped cell aggregate was observed in the case of convex ridge portions with 10-μm intervals. In a pattern with 30-μm intervals and a pattern with 40-μm intervals, substantially no adhesion between aggregates was observed. In a pattern with 5-μm intervals, cells adhered to each other across a concave groove at a high frequency; and a net-shaped cell aggregate was obtained by removing cell aggregates at a decreased temperature. A string-shaped cell aggregate was observed in the case of convex ridge portions with 10-μm intervals. In a pattern with 30-μm intervals and a pattern with 40-μm intervals, substantially no adhesion between aggregates was observed. |
| Comparative example | — | — | — | The results and the structure were the same as those described in table 3. |

Preparation of String-Shaped Primary Cardiomyocyte Aggregates on a Cell Culture Support Primary cardiomyocytes were collected and adjusted by the method of T. Shimizu et al., Circ Res. Feb. 22, 2002; 90 (3): e40. Cells were seeded in an amount sufficient to allow them to become confluent on a convex-concave substrate portion subjected to pattern coating according to the above pattern coating procedures. Culture was carried out in a chamber in the presence of 5% $CO_2$ at 37° C. for 4 days.

Specifically, the cardiac ventricles of a 1-day-old Wister rat (Nisseizai) were collected and cell separation was carried out with the use of a Hanks' solution containing collagenase (a class II cell culture reagent, Worthington). The obtained cells were seeded in a culture dish (Falcon 3002/Becton, Dickinson and Company) containing 6% fetal calf serum, 40% 119 medium (GIBCO), 0.2% penicillin/streptomycin solution, 2.7 mmol/L glucose, and a 54% balanced salt solution, followed by culture. The convex-concave substrate subjected to pattern coating according to the above pattern coating procedures was placed on the bottom of the culture dish with the cell-adherent and non-cell-adherent pattern region side up. The number of seeded cells was $8 \times 10^6$. After seeding, the culture dish was placed in a chamber in the presence of 5% $CO_2$ at 37° C., followed by culture for 4 days.

Cells that had been prepared from the baby rat myocardium adhered exclusively to the upper surface of each convex ridge portion of a convex-concave substrate portion subjected to pattern coating. Spontaneous beating was confirmed. The substrate was placed in a chamber in the presence of 5% $CO_2$ at 20° C. such that beating cells connected to each other in a string form were removed therefrom. Table 5 shows the results of each experiment.

TABLE 5

| | Width of a convex ridge portion (μm) | Distance between convex ridge portions (μm) | Depth of a concave groove (μm) | Results |
|---|---|---|---|---|
| Example 1-2 | 20 | 30 | 8 | Cell adhesion was observed mainly on the upper surface of a convex ridge portion. On day 2 of culture, action potential transmission was observed in the longitudinal direction. String-shaped cell aggregates capable of dilating and contracting in the longitudinal direction were obtained by removing cell aggregates at a decreased temperature. Substantially no adhesion between cell aggregates formed on neighboring convex ridge portions was observed. |
| Example 2-2 | 20 | 20 | 8 | Cell adhesion was observed mainly on the upper surface of a convex ridge portion. On day 2 of culture, action potential |

TABLE 5-continued

| | Width of a convex ridge portion (μm) | Distance between convex ridge portions (μm) | Depth of a concave groove (μm) | Results |
|---|---|---|---|---|
| | | | | transmission was observed in the longitudinal direction. String-shaped cell aggregates capable of dilating and contracting in the longitudinal direction were obtained by removing cell aggregates at a decreased temperature. Adhesion between cell aggregates formed on neighboring convex ridge portions was observed in every 500-μm area. |
| Example 3-2 | 20 | 10 | 8 | Cell adhesion was observed mainly on the upper surface of a convex ridge portion. On day 3 of culture, action potential transmission was observed in the longitudinal direction. String-shaped cell aggregates capable of dilating and contracting in the longitudinal direction were obtained by removing cell aggregates at a decreased temperature. Adhesion between cell aggregates formed on neighboring convex ridge portions was observed in every 100-μm area. |
| Example 4-2 | 10 | 30 | 8 | Cell adhesion was observed mainly on the upper surface of a convex ridge portion. On day 2 of culture, action potential transmission was observed in the longitudinal direction. String-shaped cell aggregates capable of dilating and contracting in the longitudinal direction were obtained by removing cell aggregates at a decreased temperature. Substantially no adhesion between cell aggregates formed on neighboring convex ridge portions was observed. |
| Example 5-2 | 10 | 20 | 8 | Cell adhesion was observed mainly on the upper surface of a convex ridge portion. On day 2 of culture, action potential transmission was observed in the longitudinal direction. String-shaped cell aggregates capable of dilating and contracting in the longitudinal direction were obtained by removing cell aggregates at a decreased temperature. Adhesion between cell aggregates formed on neighboring convex ridge portions was observed in every 500-μm area. |
| Example 6-2 | 10 | 10 | 8 | Cell adhesion was observed mainly on the upper surface of a convex ridge portion. On day 3 of culture, action potential transmission was observed in the longitudinal direction. String-shaped cell aggregates capable of dilating and contracting in the longitudinal direction were obtained by removing cell aggregates at a decreased |

TABLE 5-continued

| | Width of a convex ridge portion (μm) | Distance between convex ridge portions (μm) | Depth of a concave groove (μm) | Results |
|---|---|---|---|---|
| | | | | temperature. Adhesion between cell aggregates formed on neighboring convex ridge portions was observed in every 100-μm area. |
| Example 7-2 | 5-40 | 20 | 8 | In all patterns with 5 μm- to 40 μm-wide convex ridge portions, cell adhesion was observed on the upper surface of each convex ridge portion. On day 2 of culture, action potential transmission was observed in the longitudinal direction. String-shaped cell aggregates capable of dilating and contracting in the longitudinal direction were obtained by removing cell aggregates at a decreased temperature. Adhesion between cell aggregates formed on neighboring convex ridge portions was observed in every 500-μm area. |
| Example 8-2 | 20 | 5-40 | 8 | In a pattern with 5-μm intervals, cells adhered to each other across a concave groove at a high frequency. On day 2 of culture, action potential transmission was observed in the longitudinal direction. A net-shaped cell aggregate was obtained by removing cell aggregates at a decreased temperature. A string-shaped cell aggregate was observed in the case of convex ridge portions with 10-μm intervals. In a pattern with 30-μm intervals and a pattern with 40-μm intervals, substantially no adhesion between aggregates was observed. String-shaped cell aggregates capable of dilating and contracting in the longitudinal direction were obtained in patterns other than those having 5 μm- and 10 μm-wide concave grooves. |
| Comparative example | — | — | — | Cell adhesion was observed in the entire surface. On day 2 of culture, action potential transmission was detected and beating was observed; however, both were not directional. A plurality of pathways for action potential transmission were observed even on day 4. A cell sheet having no incisions was obtained by removing cell aggregates at a decreased temperature. The dilation and contraction of the cell sheet lacked direction. |

What is claimed is:

1. A cell culture support for forming string-shaped cardiomyocyte aggregates comprising a substrate having:
    a plurality of convex ridge portions, each having a linear, planar and reversibly cell-adherent upper surface, and
    a plurality of linear concave grooves, wherein the inner surface of each groove is non-cell-adherent.

2. The cell culture support according to claim 1, wherein the width of the linear, planar cell-adherent upper surface is 1 to 19 times wider than that of a cell to be cultured.

3. The cell culture support according to claim 1, wherein the width of the linear cell-adherent upper surface is 5 to 40 μm.

4. The cell culture support according to claim 1, wherein each of said linear convex ridge portions is separated from the other by one of the linear concave grooves.

5. The cell culture support according to claim 4, wherein the distance between two adjacent linear convex ridge portions is at least about 20 μm.

6. The cell culture support according to claim 4, wherein said concave groove is at least about 4 microns in depth.

7. The cell culture support according to claim 1, wherein the linear planar cell-adherent upper surface of each convex ridge portion is coated with an environmentally-responsive high molecular compound that has cell adhesion properties under cardiomyocyte culture conditions.

* * * * *